United States Patent [19]

Campbell et al.

[11] Patent Number: 5,788,692
[45] Date of Patent: Aug. 4, 1998

[54] MAPPING ABLATION CATHETER

[75] Inventors: Thomas H. Campbell, San Carlos; Peter Sturzu, Cupertino; Fred R. Seddiqui, Los Altos; R. Hardwin Mead, Palo Alto, all of Calif.

[73] Assignee: Fidus Medical Technology Corporation, Fremont, Calif.

[21] Appl. No.: 497,941

[22] Filed: Jun. 30, 1995

[51] Int. Cl.⁶ .......................... A61B 17/39; A61B 5/042; A61N 5/02

[52] U.S. Cl. .............. 606/33; 606/41; 600/374; 607/101; 607/156

[58] Field of Search ................ 128/642; 606/33, 606/41; 607/100–102, 113, 156; 600/374, 381

[56] References Cited

U.S. PATENT DOCUMENTS

| | | | |
|---|---|---|---|
| 4,073,287 | 2/1978 | Bradley et al. | 128/2 R |
| 4,476,872 | 10/1984 | Perlin | 128/642 |
| 4,611,604 | 9/1986 | Botvidsson et al. | 128/784 |
| 5,044,375 | 9/1991 | Bach, Jr. et al. | 128/786 |
| 5,344,441 | 9/1994 | Gronaver | 607/102 |
| 5,374,287 | 12/1994 | Rubin | 607/131 |
| 5,398,683 | 3/1995 | Edwards et al. | 128/642 |
| 5,405,346 | 4/1995 | Grundy et al. | 606/33 |
| 5,405,375 | 4/1995 | Ayers et al. | 128/642 |
| 5,417,208 | 5/1995 | Winkler | 128/642 |
| 5,450,846 | 9/1995 | Goldreyer | 128/642 |
| 5,545,193 | 8/1996 | Fleischman et al. | 606/41 |

FOREIGN PATENT DOCUMENTS

| | | | |
|---|---|---|---|
| 9402204 | 3/1994 | WIPO | 607/101 |

*Primary Examiner*—Lee S. Cohen
*Attorney, Agent, or Firm*—Beyer & Weaver, LLP

[57] ABSTRACT

A variety of improved ablation catheters and methods for using such catheters are described. In one embodiment, the catheter includes a plurality of longitudinally spaced split electrode bands that are provided near the distal end of the catheter to monitor electrophysiological signals in the patient. The electrode bands each include a plurality of electrically isolated electrode segments. The number of electrode segments in each band may be widely varied, as may the number of electrode bands. In another embodiment, the catheter has a transducer that is movable longitudinally relative to the flexible tubular member. In one embodiment, the transducer is carried at the distal end of the transmission line and the transmission line is slideably received within the flexible tubular member such that the transducer can be positioned longitudinally relative to the electrode bands. In still another embodiment, the electrodes are ion implanted on the flexible tubular member. The described catheter is introduced into a patient's body such that a distal portion of the catheter is positioned in a vessel or chamber of an organ such as the heart. The electrodes are used to monitor electrophysiological signals and an appropriate ablation position is identified based at least in part on the monitored electrophysiological signals. The transducer is then positioned at the identified ablation position and electromagnetic energy is applied to a transducer through a transmission line to cause ablation of tissue in a region adjacent the identified ablation position.

10 Claims, 7 Drawing Sheets

MAPPING ABLATION CATHETER

BACKGROUND OF THE INVENTION

The present inventions relate generally to ablation catheters having monitoring electrodes thereon. More particularly, an ablation catheter having split electrode rings is described.

Catheter ablation has recently become an important therapy for certain cardiac arrhythmias, cardiac disrhythmias and tachycardia. Most approved ablation catheter systems now utilize radio frequency (RF) energy as the ablating energy source. However, there are a number of catheters under development which utilize electromagnetic energy in the microwave frequency range as the ablation energy source. By way of example, such systems are described in the U.S. Pat. Nos. 4,641,649 to Walinsky; 5,246,438 to Langberg; 5,405,346 to Grundy, et al.; and 5,314,466 to Stern, et al, each of which is incorporated herein by reference.

During positioning and/or use of the ablation catheter, it is often desirable to monitor certain electrophysiological properties of the heart. To facilitate such electrophysiological monitoring, electrodes are often positioned near the distal end of the catheter. Typically, such electrodes take the form of either annular metallic rings and/or a distally positioned electrode. Although such electrode based monitoring systems have worked in the past, there are continuing efforts to improve their functionality.

In many application it is desirable to "map" a region of the heart prior to an ablation operation in order to help locate the portion of the cardiac tissue which is to be ablated. Since conventional ablation catheter electrode structures are typically not well adapted for mapping, separate mapping catheters are sometimes used prior to an ablation operation to map the portions of the cardiac tissue that are of interest. After the region has been mapped, the mapping catheter is withdrawn and a separate ablation catheter is inserted in its place to accomplish the ablation operation. Such dual catheter insertion procedures increase the length of the operation as well as the amount of catheter equipment desired, it would be desirable to have a catheter that is particularly effective at both ablation and mapping.

SUMMARY OF THE INVENTION

To achieve the foregoing and other objects and in accordance with the purpose of the present invention, a variety of improved ablation catheters and methods for using such catheters are described. In various apparatus aspects of the invention, the catheter includes an elongated flexible tubular member adapted to be inserted into a vessel in the body of a patient. A transmission line suitable for transmitting electromagnetic energy is received within the tubular member. A transducer is coupled to the transmission line for generating an electric field sufficiently strong to cause tissue ablation.

In one aspect of the invention, the catheter includes a plurality of longitudinally spaced split electrode bands that are provided near the distal end of the catheter to monitor electrophysiological signals in the patient. In this aspect, the electrode bands each include a plurality of electrically isolated electrode segments. The number of electrode segments in each band may be widely varied, as may the number of electrode bands.

In another aspect of the invention, the transducer is movable longitudinally relative to the flexible tubular member. In one embodiment, the transducer is carried at the distal end of the transmission line and the transmission line is slideably received within the flexible tubular member such that the transducer can be positioned longitudinally relative to the electrode bands.

In still another aspect of the invention, the electrodes are ion implanted on the flexible tubular member. A wide variety of materials can be used to form the electrodes, such as silver, stainless steel, platinum, etc. When ion implanted electrodes are used, the electrodes themselves are flexible, which improves the overall flexibility of the catheter's distal portion.

In a method aspect of the invention the catheter is introduced into a patient's body such that a distal portion of the catheter is positioned in a vessel or chamber of an organ such as the heart. Catheter electrodes are used to monitor electrophysiological signals and an appropriate ablation position is identified based at least in part on the monitored electrophysiological signals. A transducer is then positioned at the identified ablation position and electromagnetic energy is applied to a transducer through a transmission line to cause ablation of tissue in a region adjacent the identified ablation position. In some embodiments, the transducer positioning step includes at least one of further inserting the catheter or partially withdrawing the catheter to position the transducer. In other embodiments, the transducer positioning step includes the substep of moving the transducer relative to the catheter tubing.

These different aspects of the invention may be used alone or in combination and the described inventions are all well suited for use in microwave ablation catheter systems.

BRIEF DESCRIPTION OF THE DRAWINGS

The inventions, together with further objects and advantages thereof, may best be understood by reference to the following description taken in conjunction with the accompanying drawings in which.

DETAILED DESCRIPTION OF THE INVENTION

Figure 1A:
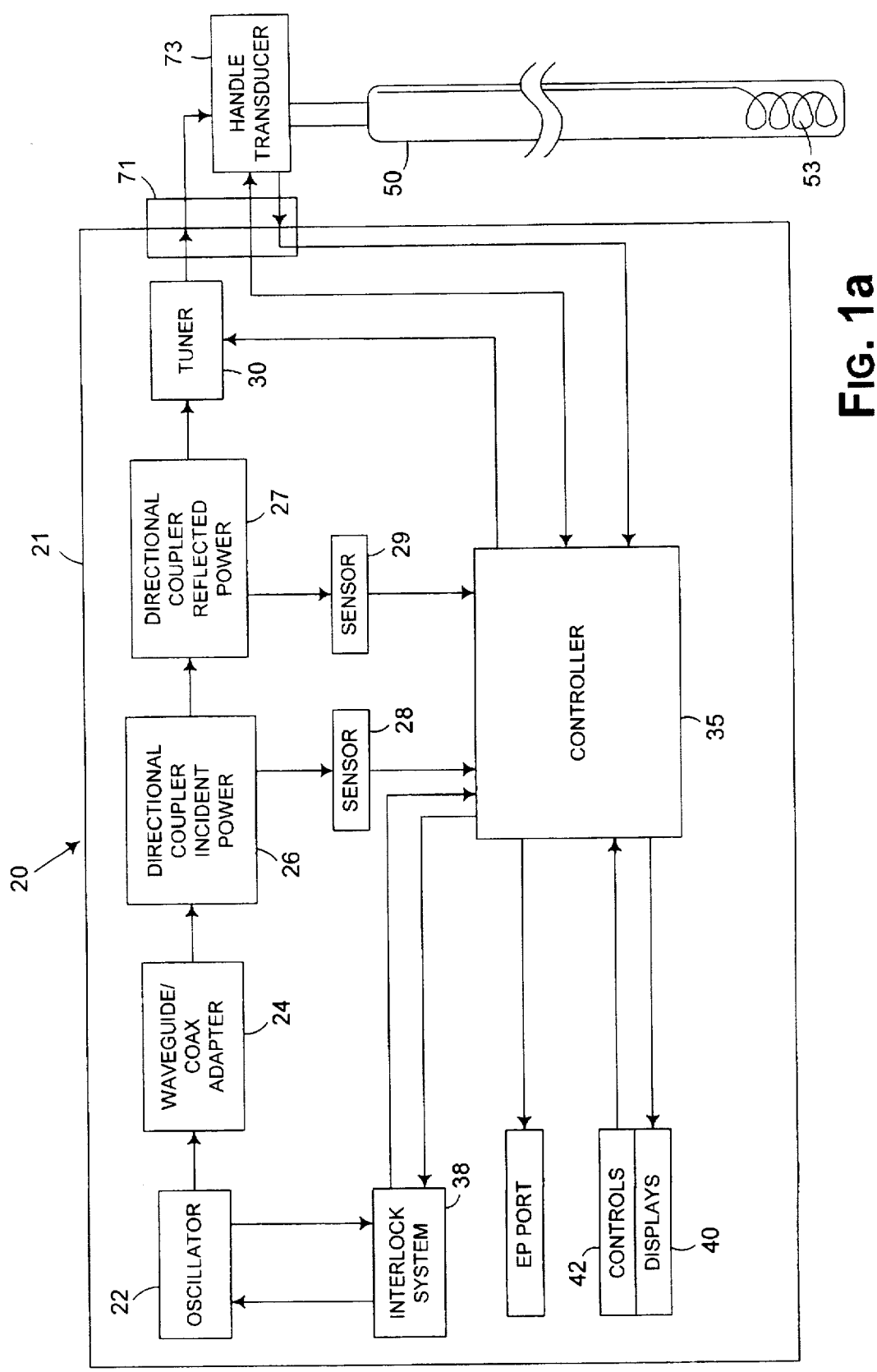
FIG. 1a is a diagrammatic illustration of a microwave ablation catheter system in accordance with one embodiment of the present invention.

Several presently preferred ablation catheter systems in accordance with the present invention will be described below making reference to the accompanying drawings. As seen in FIG. 1a, an ablation catheter system 10 generally includes a power supply 20 which is designed to generate controlled electromagnetic energy, a catheter 50 which is designed for insertion into a vessel (such as a coronary vessel) in the body of a patient and a connector 71 for coupling the power supply 20 to the catheter 50.

Figure 1B:
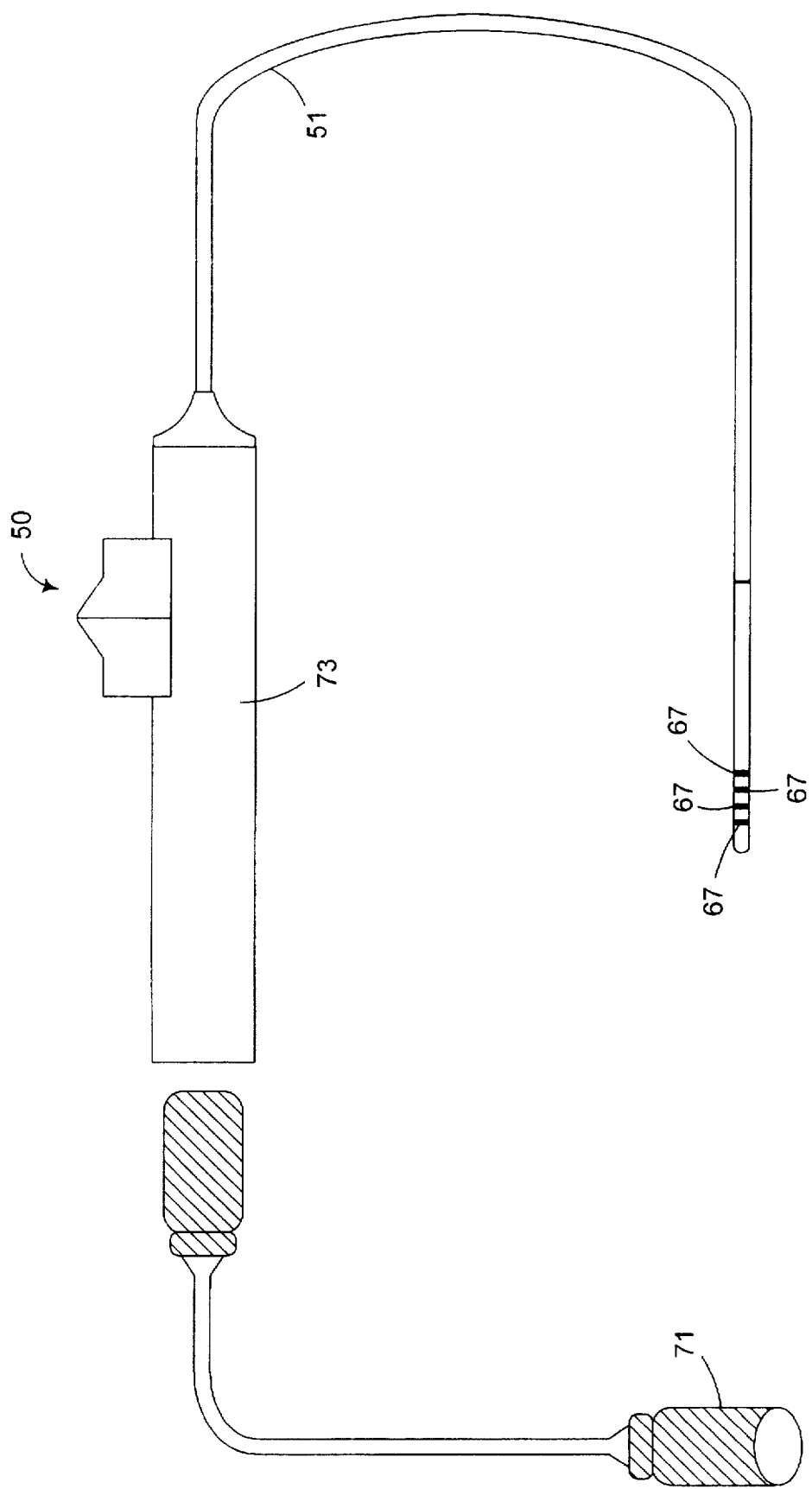
FIG. 1b is a diagrammatic perspective illustration of a microwave ablation catheter in accordance with one embodiment of the present invention.
Figure 2:
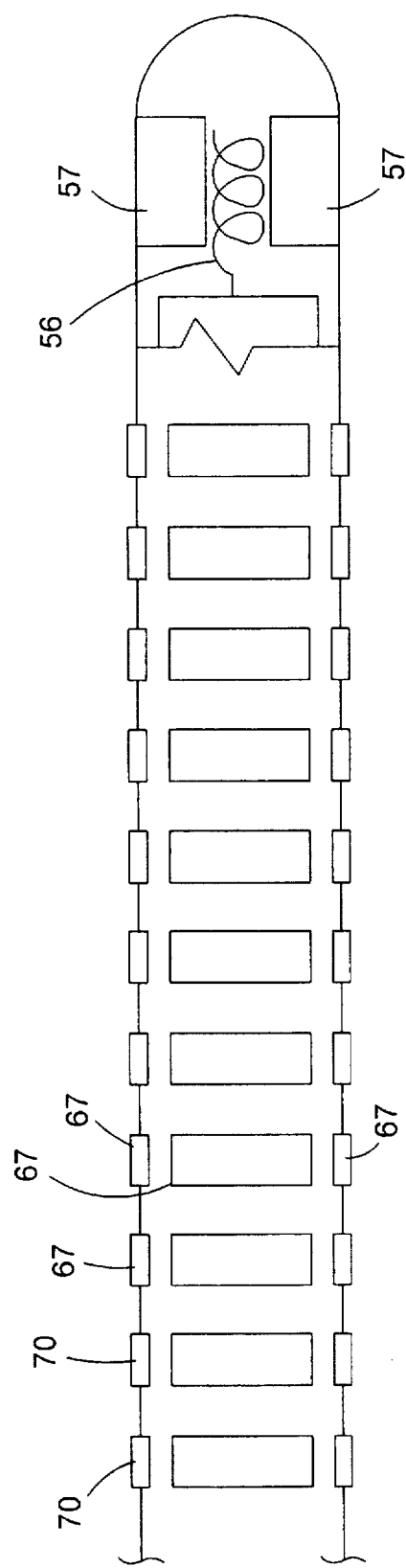
FIG. 2 is a diagrammatic side view of the distal end portion of another ablation catheter having four segment electrode bands, with the antenna portion cut away and schematically represented.

Referring next to FIGS. 1b and 2, the catheter 50 includes a flexible outer tubing 51, a coaxial transmission line 53, a transducer 56, a series of electrode bands 67 and a connector 71. Each of the electrode bands 67 has a plurality of electrode segments 70. Each electrode segment has an associated electrode wire 61. The electrode bands 67 are provided near the tip of the catheter to detect electrophysiological signals from the cardiac tissue and therefore can be used to map the relevant region of the heart prior to or after an ablation procedure. The electrodes may also be used to monitor the patient's condition during the ablation process. In the described embodiment, the information obtained from the electrodes segments 70 is transmitted via the electrode wires 61, through connector 70 and through the power supply 20 to external electronics such as an EP signal monitoring device. Filtering of the signal may be provided as necessary. In alternative embodiments, some of the external electronics could be incorporated into the power supply and/or the power supply could use information obtained from the electrodes in its control scheme.

Figure 4:
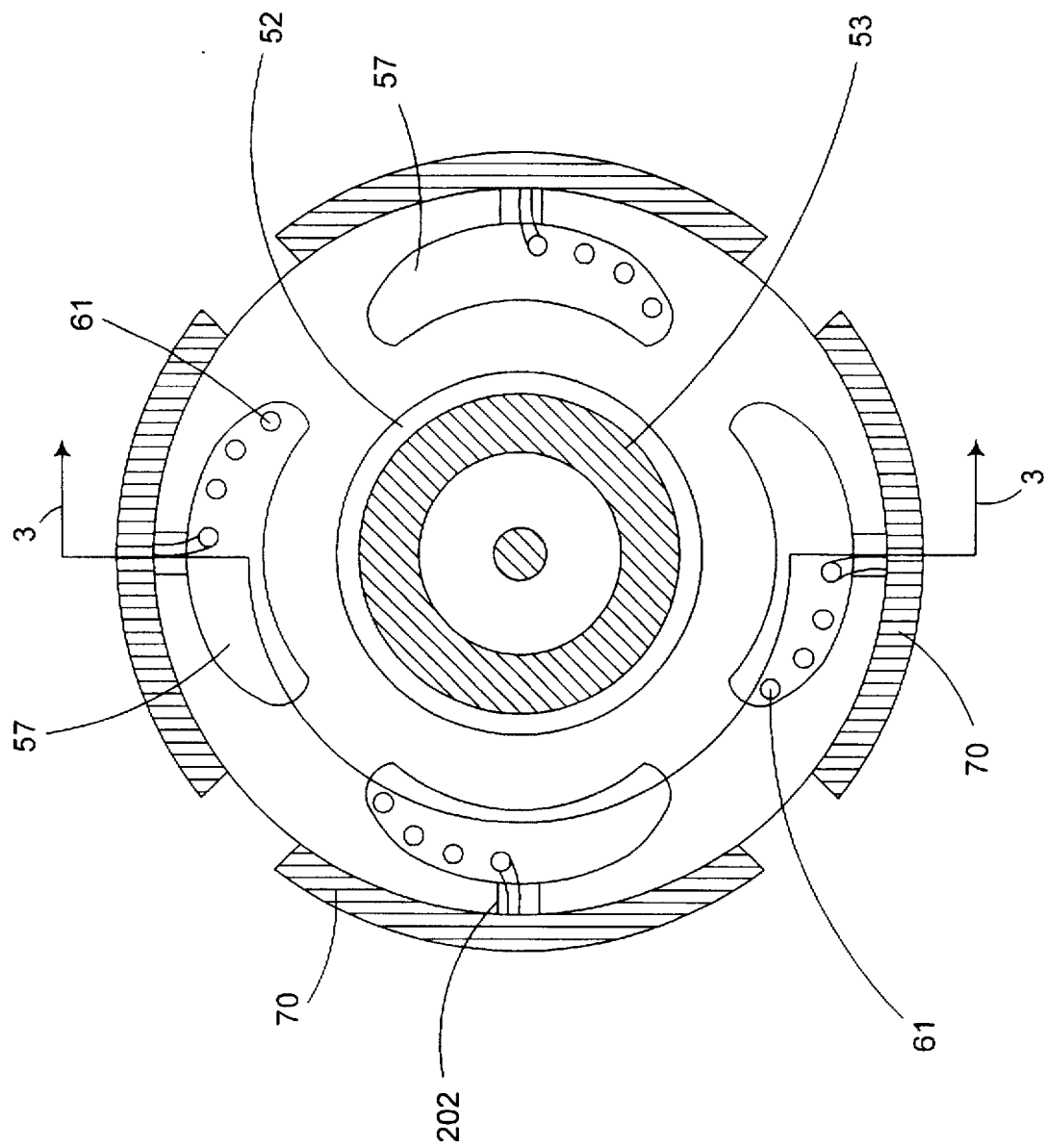
FIG. 4 is a diagrammatic cross sectional view of a flexible tubular member having a central lumen adapted to receive the wave guide and for peripheral lumens adapted to receive various electrode wires.

As best seen in FIG. 2, the outer flexible tubing member 51 in the embodiment shown includes an elongated tube portion 54 and a distal cap 63. As shown in FIG. 4, the tube portion 54 has an enlarged central lumen 52, and a plurality of peripheral lumens 57. The central lumen 52 is sized to receive the coaxial transmission line 53. Electrode wires 61 and various other wires such as thermometry wires, steering wires and stiffening wires (not shown) may be run through the peripheral lumens 57. The outer tubing 51 may be made of any suitable material such as medical grade polyolefins, fluoropolymers, or polyvinylidene fluoride. By way of example, PEBAX resins from Autochem of Germany have been used with success for the outer tubing of the body of the catheter. However, Teflon type products are preferred for the distal cap 63. The connector 71 couples the transmission line 53 to the external power supply 20.

As is best illustrated in FIG. 2, each electrode band 67 has a plurality of electrically isolated electrode segments 70. It has been found that splitting the electrode bands into a plurality of distinct elements permits substantially improvements in the resolution of the detected electrophysiological signals. In the embodiment shown, each band includes four isolated electrodes. However, in alternative embodiment, the number of isolated electrode segments per band may be any number that is two or greater. The actual number of bands and their relative spacing may also be widely varied. By way of example, numbers in the range of 2 to 64 bands work well. In the embodiment shown in FIG. 1b, four electrode bands are shown. In the embodiment shown in FIG. 2, eleven electrode bands are provided. Additionally, a pair of distal electrodes 57 may optionally be provided in the antenna region. Such distal electrodes are particularly desirable in end fire antenna configurations.

The electrodes may be formed from any suitable material such as 300 series stainless steel, platinum or silver. One approach to forming the electrode bands is to install a series of annular metal bands 67 at spaced locations on the catheter tip. The bands 67 are then cut to electrically isolate the segments 70. When this approach is used, the gap 69 between adjacent segments 70 may be fairly narrow, as for example on the order of 25 to 35 thousandths of an inch (approximately 0.6 to 0.9 mm). Another approach is to individually attach metallic electrode segments 70 to their associated electrode wires 61 and install the electrode wires as will be described in more detail below.

As will be appreciated by those skilled in the art, in coronary applications, the catheter diameter is typically limited to approximately 7½ French (approximately 2.5 mm in diameter). In microwave ablation catheter systems it is important to use a coaxial transmission line that is not too small in diameter to insure that the attenuation within the catheter is not too large. By way of example, coaxial transmission lines that are on the order of 72 mils in diameter (1.8 mm) tend to work well in microwave ablation catheter systems. Thus, a substantial portion of the catheter diameter is taken up by the coaxial transmission line and the outer diameter of the electrode bands (which is typically the diameter of the catheter itself) is generally over approximately 2.0 mm. Thus, when solid metal bands or electrodes are used, it is important that the longitudinal electrode length be kept relatively short so that the catheter's flexibility is not too adversely effected. By way of example, a typical electrode band may have an inner diameter on the order of 85 to 90 mils (2.1 to 2.25 mm), an outer diameter on the order of 95 to 100 mils (2.4 to 2.5 mm) and have a longitudinal length on the order of 50 to 60 mils (1.25 to 1.5 mm). Of course, these dimensions can be varied to meet the needs of any particular catheter design. The spacing between adjacent electrode bands can also be widely varied. By way of example, spacings on the order of 120 to 200 mils (3 to 5 mm) work well.

Figure 3:
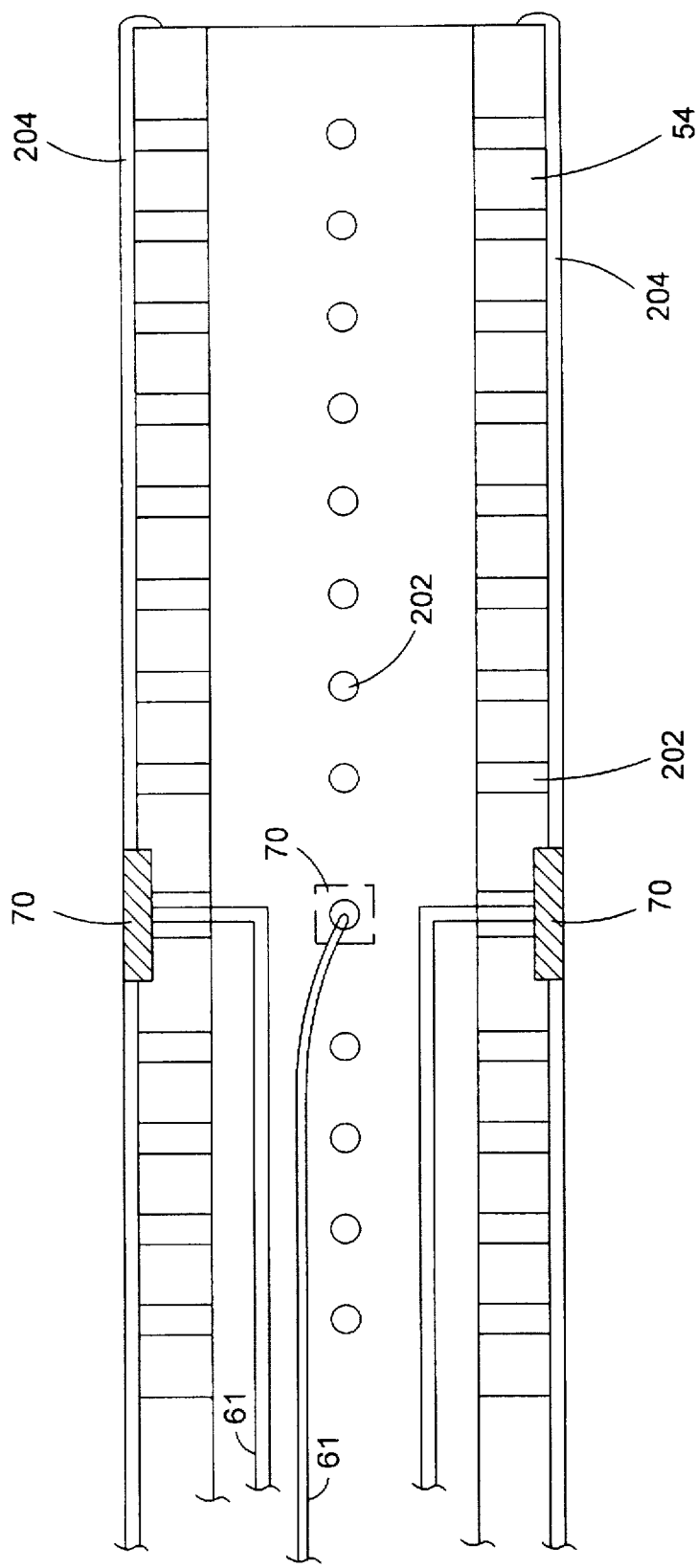
FIG. 3 is a diagrammatic illustration of an arrangement for attaching electrodes to a catheter using shrink wrap tubing.
Figure 5:
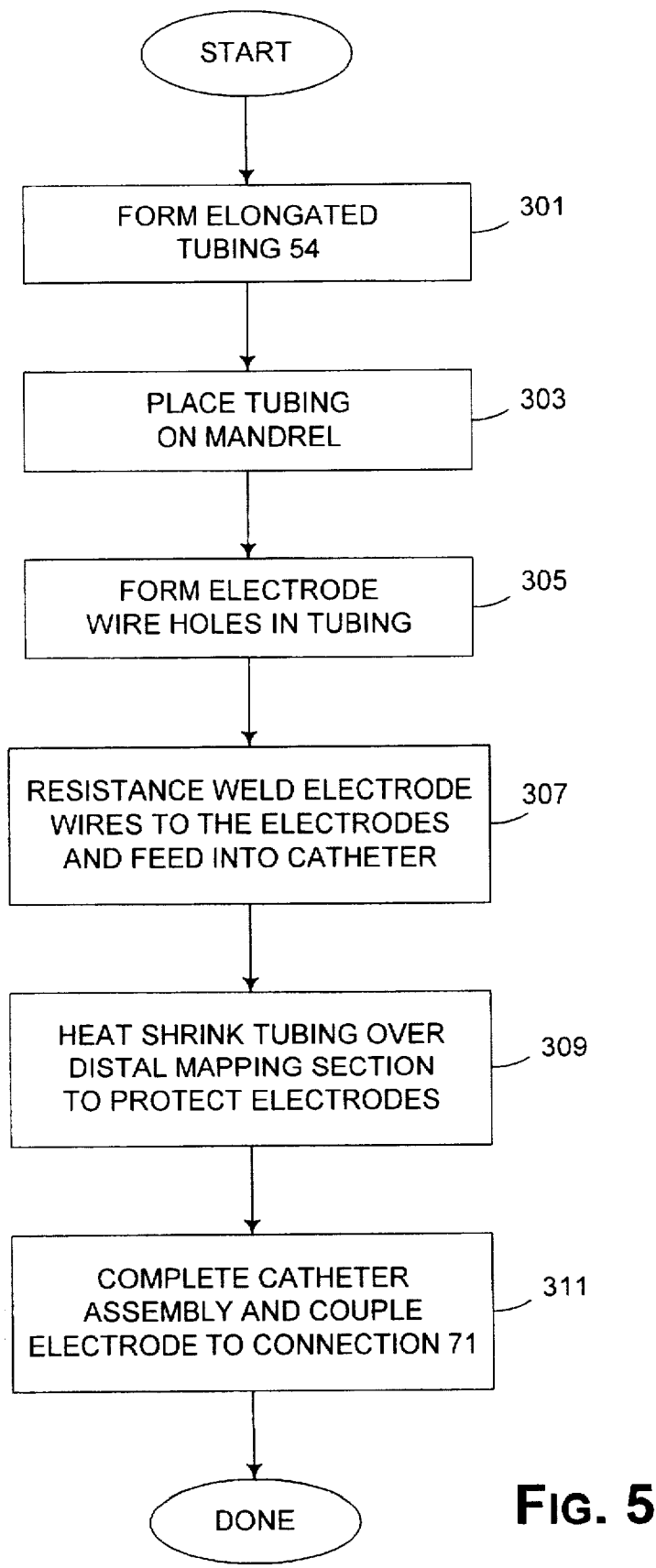
FIG. 5 is a flow chart illustrating steps in a process for installing the electrodes of a catheter in accordance with one embodiment of the present invention.

Referring next to FIGS. 3–5, a process suitable for installing the electrodes will be describe. FIGS. 3 and 4 diagrammatically illustrate the construction of the flexible tubular member. More specifically, FIG. 4 is a cross sectional view of the catheter. FIG. 3 is a partially cut away side view of the flexible tubing 54 itself taken along line 3—3 of FIG. 4. For clarity, only the tubing 54, one band of electrodes and a protective heat shrink tubing 204 are shown. FIG. 5 is a flow chart illustrating the relevant steps in a process for installing the electrodes of a catheter in accordance with one embodiment of the present invention.

Referring initially to FIG. 5, the process begins at step 301 when an elongated tube 54 is formed. In the embodiment shown in FIG. 4, the tube 54 includes an enlarged central lumen 52 sized to receive the coaxial transmission line 53, and a plurality of peripheral lumens 57. The tube 54 is installed on a mandrel in step 303. Thereafter, a series of electrode wire holes 202 are formed in the tube 54 in step 305. An electrode wire hole 202 is provided for each electrode segment 70. Independently, the electrode segments 70 are each resistance welded to an associated electrode wire 61. The assembled structures are then fed into the tubing 54 in step 307. Specifically, the electrode wires 61 are fed through their associated electrode wire holes 202 and pulled tight so that their associated electrode segments are pulled tight against the surface of the tubing 54. It should be appreciated that the electrodes may either be installed as annular bands that are cut into segments after they are installed, or as independent segments that form associated bands only after installation.

After all of the electrode segments have been secured in step 307, a protective electrode coating is provided in step 309. In the described embodiment, a heat shrink tubing 204 is placed over the various electrodes which collectively are referred to as the distal mapping section of the catheter. The heat shrink tubing is then heated and shrunk so that it tightly covers the electrode segments 70 and seals the electrode wire holes 202. At this point the electrodes have effectively been installed. After the electrodes have been installed, they are coupled to the connector 71 and the remainder of the catheter is fabricated in step 311. The actual steps involved in completing the assembly of the catheter will vary a great deal in accordance with the design of any particular catheter. By way of example, a distal cap that houses an antenna assembly coupled to a co-axial cable may be attached to the distal end of the tubing 54 and the proximal ends of the various wires may be attached to the connector 71.

In an alternative preferred embodiment of the invention, the electrode material is directly ion implanted on the flexible tubular member. One significant advantage of the ion implantation approach is that the arcuate electrodes themselves are essentially as flexible as the tubular member and thus do not inhibit the catheter's maneuverability regardless of the electrode dimensions. This even further improves the maneuverability of the catheter tip and permits the use of electrodes of any desired size since it is relatively easy to control the electrode dimensions in the ion implantation process.

A wide variety of implantable electrode materials can be used. By way of example, ion implanted silver has good biocompatibility and is therefor useful in embodiments in which the electrodes are formed on the exterior surface of the tubular member 51. Suitable ion implantation services are available from Spire Corporation of Bedford, Mass.

One method for using the described catheter in a coronary ablation procedure will now be described. The catheter may be fed through the femoral artery or other suitable vessel and into the appropriate region of the heart. By way of example, to treat ventricular tachycardia, the catheter tip is typically feed into the appropriate ventricle chamber. With the catheter properly positioned, the electrodes can detect electrical signals in the adjacent regions of the heart. Thus, the various electrodes are monitored to effectively "map" the region of the heart of interest. If necessary, the catheter can be further inserted, and or withdrawn to further facilitate mapping the region of interest.

Typically, the mapping will indicate the location at which desired signals are the strongest, which will permit the physician to determine the appropriate ablation position. The catheter is then withdrawn or further inserted as necessary to position the antenna properly for the ablating procedure. After the antenna is properly positioned, microwave energy is applied to the co-axial transmission line to facilitate the ablation. During the ablation procedure, as well as after the operation is completed, the electrodes may be used to monitor the ablation process as well as the results. When desirable, the catheter can be further positioned after the ablation procedure to facilitate post procedure mapping. If necessary, further ablation can be thereafter carried out in a similar manner. It should be appreciated that the direction that the microwave energy is directed can be controlled to a great extent based on the design of the antenna. The described arrangements may be used in conjunction with a wide variety of transducer/antenna designs.

Figure 6:
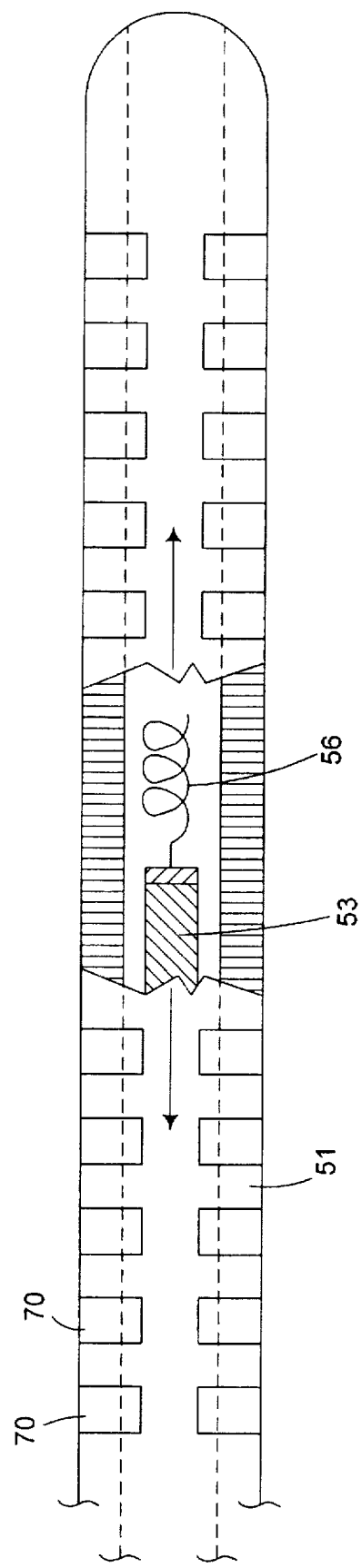
FIG. 6 is a diagrammatic partially broken away side view of the distal end portion of a second embodiment of the present invention which includes a longitudinally movable antenna assembly.

Referring next to FIG. 6 an alternative embodiment of the present invention which features a longitudinally slideable antenna assembly will be described. In this embodiment, a longitudinally extending helical antenna 56 is carried at the distal end of the coaxial transmission line 53. The antenna 56 takes the form of a coiled extension of the transmission line's center conductor. In this embodiment, the coaxial cable 53 is slideably received within the central lumen 52 of flexible tubular member 51. The handle 73, shown in FIG. 1a, includes a finger actuated slider with a slider lock (not shown) that the doctor may use to slide the coaxial cable relative to the tubular member 51. In other respects the catheter design may be similar to the design described above. The advantage of this structure is that after the mapping has been accomplished, the antenna and transmission line assembly alone (as opposed to the entire catheter) may be moved to position the transducer in the appropriate ablation position. The reduced movement is more comfortable to the patient, and since the catheter remains fixed, it may prove easier to precisely position the antenna in the desired position.

It is noted that the described longitudinally extending helical coil tends to generate a field that extends laterally from the catheter. Although the electrodes will have some effect on the shape and penetration of the field generated by the antenna, they do not prevent its use. In some embodiments which have relatively well spaced electrodes, it may be desirable to try to center the antenna position in the spacing between adjacent electrode bands. However, this is not a requirement.

Referring next to FIG. 1a, a suitable power supply 20 will be described. However, it should be appreciated that the nature and design of the power supply may be widely varied and is not particularly relevant to the present invention. In the embodiment shown, the power supply 20 includes a casing 21 having a microwave generator 22, a waveguide adapter 24, a pair of directional couples 26 & 27 that interface with power sensors 28 & 29, a tuner 30, a controller 35 and an interlock system 38 all enclosed therein. The front panel (now shown) of the casing has various displays 40 and controls 42, as well as a port 43 to which conventional EP signal monitoring equipment can be coupled. It is with this EP signal monitoring equipment that the electrode wires would typically be in electrical communication.

The microwave generator 22 may take any conventional form. When using microwave energy for tissue ablation, the optimal frequencies are generally in the neighborhood of the optimal frequency for heating water. By way of example, frequencies in the range of approximately 800 MHz to 3 GHz work well. At the time of this writing, the frequencies that are approved by the U.S. Food and Drug Administration for experimental clinical work are 915 MHz and 2.45 GHz. Therefore, a power supply having the capacity to generate microwave energy at frequencies in the neighborhood of 2.45 GHz may be chosen. At the time of this writing, solid state microwave generators in the 1–3 GHz range are very expensive. Therefore, a conventional magnetron of the type commonly used in microwave ovens is utilized as the generator. It should be appreciated, however, that any other suitable microwave power source could be substituted in its place.

The microwave energy is transmitted from the microwave generator 22 through a waveguide and coax adapter 24 to a pair of directional couplers 26 & 27 used to monitor forward and reflected power respectively. The output of each directional coupler is connected to an associated power sensor 28 or 29 which output signals indicative of the forward and reflected power to the controller. It is contemplated that other suitable power monitors could be used in place of the described directional coupler/power sensor arrangements. Following the directional couplers, the transmission line may be equipped with a tuner mechanism 30 that is controlled by the controller 35 to facilitate impedance matching throughout the catheter system. In alternative embodiments, a tuning mechanism may be provided in the catheter as described in U.S. Pat. No. 5,405,346. Downstream from the tuner 30, the power is directed through a quick disconnect jack and plug (connector 71) to the catheter 50 itself. System controls are provided for operation of the power supply as is a display for displaying such information as system set points, forward and reflected power, temperatures, etc. The controller 35 may take the form of dedicated logic, but in a preferred embodiment a conventional microprocessor or computer is used.

Although only a few embodiments of the present inventions have been described in detail, it should be understood that the present inventions may be embodied in many other specific forms without departing from the spirit or scope of the inventions. Particularly, the invention has been described in terms of a microwave ablation catheter for cardiac applications, however, it should be appreciated that the described small diameter microwave ablation catheter could be used for a wide variety of non-cardiac ablation applications as well. Further, certain aspects of the invention have applications well beyond the field of microwave ablation catheters. By way of example, the described ion implanted electrodes may be used in a variety of catheter constructions and is not limited to ablation catheters. It is contemplated that both the catheter design and the design of the power supply may be widely modified without departing from the scope of this invention. Therefore, the present examples are to be considered as illustrative and not restrictive, and the invention is not to be limited to the details given herein, but may be modified within the scope of the appended claims.

We claim:

1. A catheter comprising:
    an elongated flexible tubular member adapted to be inserted into a vessel in the body of a patient, the flexible tubular member including a distal portion and a proximal portion;
    a coaxial transmission line disposed and slideably received within the tubular member, the transmission line having proximal and distal ends, wherein the proximal end of the transmission line is suitable for connection to a microwave energy source;
    at least eight mapping electrode bands that are longitudinally spaced along the surface of the flexible tubular member, wherein the electrode bands are ion implanted on the flexible tubular member such that the electrode bands are flexible, each of the electrode bands including a plurality of electrically isolated electrodes, the electrode bands being configured to facilitate the mapping of the tissues adjacent to the catheter to identify a location of tissue to be ablated;
    a plurality of electrode wires each electrically coupled to one of the plurality of electrically isolated electrodes of the at least eight electrode bands and extending through to the proximal portion of the flexible tubular member; and
    a microwave antenna coupled to the distal end of the transmission line for generating an electromagnetic field of energy sufficiently strong to cause tissue ablation, the antenna being received and longitudinally slideable within the flexible tubular member together with the transmission line, such that longitudinal movement of the coaxial transmission line within the flexible tubular member causes the longitudinal movement of the antenna within the flexible tubular member such that the antenna may be positioned longitudinally relative to the plurality of mapping electrode bands, whereby during use the tubular member may be positioned within the vessel and a portion of the vessel mapped using the electrodes to facilitate the identification of tissue to be ablated, and after the mapping has been accomplished the antenna and transmission line may be longitudinally slid, relative to the electrodes, within the tubular member to position the antenna appropriately for ablation of the identified tissue without requiring the movement of the flexible tubular member relative to the vessel after mapping to effectuate ablation.

2. A catheter as recited in claim 1 wherein each electrode band includes at least four electrically isolated electrodes.

3. A microwave ablation catheter comprising:
    an elongated flexible tubular member adapted to be inserted into a vessel in the body of a patient, the flexible tubular member including a distal portion and a proximal portion;
    a coaxial transmission line disposed and slideably received within the tubular member, the transmission line having proximal and distal ends, wherein the proximal end of the transmission line is suitable for connection to a microwave energy source;
    a plurality of mapping electrodes that are longitudinally spaced along the flexible tubular member; and
    an antenna coupled to the distal end of the transmission line for generating an electromagnetic field sufficiently strong to cause tissue ablation, the antenna being received and longitudinally slideable within the flexible tubular member together with the transmission line, such that the antenna may be positioned longitudinally relative to the plurality of mapping electrodes wherein the range of movement of the antenna permits the antenna to be slid back and forth past the mapping electrodes whereby during use the tubular member may be positioned within the vessel and a portion of the vessel mapped to facilitate the identification of tissue to be ablated, and after the mapping has been accomplished the antenna and transmission line may be longitudinally slid within the tubular member to position the antenna appropriately for ablation of the identified tissue without requiring the movement of the flexible tubular member relative to the vessel after mapping to effectuate ablation.

4. A catheter as recited in claim 3 wherein each electrode takes the form of an electrode band that includes a plurality of electrically isolated electrode segments.

5. A catheter as recited in claim 4 wherein there are at least five electrode bands.

6. A catheter as recited in claim 4 wherein there are at least eleven spaced apart electrode bands.

7. A catheter as recited in claim 4 wherein each electrode band includes at least four electrically isolated electrodes.

8. A catheter as recited in claim 3 wherein the electrodes are ion implanted on the flexible tubular member such that the electrodes are flexible.

9. A catheter as recited in claim 3 wherein there are at least four electrodes.

10. A catheter as recited in claim 3 wherein the longitudinal distance between the proximal end of a most proximal electrode of the plurality of electrodes and the distal end of a most distal electrode of the plurality of electrodes is in the range of approximately 50 mm to approximately 400 mm.

* * * * *